(12) United States Patent
Yamamoto et al.

(10) Patent No.: US 12,053,199 B2
(45) Date of Patent: Aug. 6, 2024

(54) ULTRASONIC SURGICAL IRRIGATION SLEEVE AND RELATED ASSEMBLIES

(71) Applicant: Stryker European Operations Limited, Carrigtwohill (IE)

(72) Inventors: Masaya Yamamoto, Tokyo (JP); Guillaume Gras, Muenchenbuchsee (CH); Hidefumi Ota, Yokohama (JP)

(73) Assignee: Stryker European Operations Limited, Carrigtwohill (IE)

( * ) Notice: Subject to any disclaimer, the term of this patent is extended or adjusted under 35 U.S.C. 154(b) by 570 days.

(21) Appl. No.: 17/423,338

(22) PCT Filed: Jan. 15, 2020

(86) PCT No.: PCT/IB2020/050314
§ 371 (c)(1),
(2) Date: Jul. 15, 2021

(87) PCT Pub. No.: WO2020/148681
PCT Pub. Date: Jul. 23, 2020

(65) Prior Publication Data
US 2022/0125462 A1    Apr. 28, 2022

Related U.S. Application Data

(60) Provisional application No. 62/792,571, filed on Jan. 15, 2019.

(51) Int. Cl.
*A61B 17/32* (2006.01)
*A61B 17/00* (2006.01)

(52) U.S. Cl.
CPC .......... *A61B 17/320068* (2013.01); *A61B 2017/00477* (2013.01); *A61B 2017/320082* (2017.08); *A61B 2017/320084* (2013.01)

(58) Field of Classification Search
CPC .. A61B 17/320068; A61B 2017/00477; A61B 2017/320082; A61B 2017/320084;
(Continued)

(56) References Cited

U.S. PATENT DOCUMENTS 3,805,787 A * 4/1974 Banko ............... A61M 1/85
606/171
4,223,676 A * 9/1980 Wuchinich ....... A61B 17/22012
366/127
(Continued)

FOREIGN PATENT DOCUMENTS

EP     0578376 A1    1/1994
EP     1199054 A1    4/2002
(Continued)

OTHER PUBLICATIONS

English language abstract and machine-assisted English translation for JPH 04-89042 A extracted from espacenet.com database on Oct. 19, 2023, 4 pages.
(Continued)

*Primary Examiner* — Erich G Herbermann
*Assistant Examiner* — Aman Kumar Mann
(74) *Attorney, Agent, or Firm* — Howard & Howard Attorneys PLLC

(57) ABSTRACT

An ultrasonic surgical instrument assembly including an irrigation sleeve assembly defining a lumen and an ultrasonic tip at least partially disposed within the lumen of the irrigation sleeve. The irrigation sleeve assembly may comprise a hub and an irrigation sleeve coupled to the hub. The irrigation sleeve may comprise an inner sheath and an outer sheath, both extending distally from the hub. The outer sheath may surround at least a portion of the inner sheath to define an irrigation passageway between the outer sheath and the inner sheath configured to deliver irrigation fluid to
(Continued)

the surgical site. The distal end of the inner sheath may extend beyond the distal end of the outer sheath. Each of the inner and the outer sheath may be coupled to the hub by an annular sealing member configured to create fluid-tight seal between the hub and the respective inner and outer sheath.

20 Claims, 11 Drawing Sheets

(58) Field of Classification Search
CPC . A61B 17/24; A61B 17/1644; A61B 17/1688; A61B 17/1695; A61B 2017/320069; A61B 2217/007; F16L 47/22
See application file for complete search history.

(56) References Cited

U.S. PATENT DOCUMENTS

| | | |
|---|---|---|
| 4,660,573 A | 4/1987 | Brumbach |
| 5,151,083 A | 9/1992 | Pichler |
| 5,151,084 A | 9/1992 | Khek |
| 5,163,433 A | 11/1992 | Kagawa et al. |
| 5,225,001 A | 7/1993 | Manni et al. |
| 5,255,669 A | 10/1993 | Kubota et al. |
| 5,453,087 A | 9/1995 | Malinowski |
| 5,469,853 A | 11/1995 | Law et al. |
| 5,486,162 A | 1/1996 | Brumbach |
| 5,492,527 A | 2/1996 | Glowa et al. |
| 5,516,043 A | 5/1996 | Manna et al. |
| 5,527,273 A | 6/1996 | Manna et al. |
| 5,562,609 A | 10/1996 | Brumbach |
| 5,702,360 A | 12/1997 | Dieras et al. |
| 5,782,795 A | 7/1998 | Bays |
| 6,126,592 A | 10/2000 | Proch et al. |
| 6,224,565 B1 | 5/2001 | Cimino |
| 6,270,471 B1 | 8/2001 | Hechel et al. |
| 6,282,442 B1 | 8/2001 | DeStefano et al. |
| 6,398,759 B1 | 6/2002 | Sussman et al. |
| 6,497,715 B2 | 12/2002 | Satou |
| 6,652,547 B2 | 11/2003 | Rabiner et al. |
| 6,955,680 B2 | 10/2005 | Satou et al. |
| 6,984,220 B2 | 1/2006 | Wuchinich |
| 7,018,354 B2 | 3/2006 | Tazi |
| 7,150,713 B2 | 12/2006 | Shener et al. |
| 7,247,161 B2 | 7/2007 | Johnston et al. |
| 7,608,054 B2 | 10/2009 | Soring et al. |
| 7,771,384 B2 | 8/2010 | Ravo |
| 7,918,849 B2 | 4/2011 | Bleich et al. |
| 8,162,966 B2 | 4/2012 | Connor et al. |
| 8,192,435 B2 | 6/2012 | Bleich et al. |
| 8,574,253 B2 | 11/2013 | Gruber et al. |
| 8,579,902 B2 | 11/2013 | Bleich et al. |
| 8,672,921 B2 | 3/2014 | Efinger et al. |
| 9,028,398 B2 | 5/2015 | Kumar et al. |
| 9,211,137 B2 | 12/2015 | Voic |
| 9,259,234 B2 | 2/2016 | Robertson et al. |
| 9,622,766 B2 | 4/2017 | Voic |
| 9,622,767 B2 | 4/2017 | Stoddard et al. |
| 9,872,695 B2 | 1/2018 | Riva |
| 10,092,308 B2 | 10/2018 | Mikus et al. |
| 10,166,317 B2 | 1/2019 | Banko |
| 10,207,045 B2 | 2/2019 | Banko |
| 10,299,819 B2 | 5/2019 | Akilian et al. |
| 10,342,566 B2 | 7/2019 | Stoddard et al. |
| 10,363,060 B2 | 7/2019 | Stoddard et al. |
| 10,456,156 B2 | 10/2019 | Stoddard et al. |
| 10,470,789 B2 | 11/2019 | Mikus et al. |
| 10,561,305 B2 | 2/2020 | Gerrans et al. |
| 10,799,264 B2 | 10/2020 | Inamdar et al. |
| 10,835,768 B2 | 11/2020 | Robertson et al. |
| 2003/0108844 A1 | 6/2003 | Rahman et al. |
| 2008/0058775 A1 | 3/2008 | Darian et al. |
| 2010/0036388 A1 | 2/2010 | Gomez |
| 2011/0196403 A1* | 8/2011 | Robertson ........ A61B 17/22012 606/169 |
| 2011/0270293 A1* | 11/2011 | Malla ............... A61B 17/32002 606/180 |
| 2013/0331872 A1* | 12/2013 | Parham .......... A61B 17/320068 606/169 |
| 2015/0038894 A1 | 2/2015 | Urich et al. |
| 2015/0148829 A1 | 5/2015 | Kimball et al. |
| 2015/0265305 A1* | 9/2015 | Stulen ................. A61B 17/285 606/169 |
| 2016/0128708 A1 | 5/2016 | Mikus et al. |
| 2017/0304655 A1 | 10/2017 | Cotter et al. |
| 2017/0354429 A1 | 12/2017 | Ketelhohn et al. |
| 2019/0021754 A1 | 1/2019 | Mark et al. |
| 2019/0175204 A1 | 6/2019 | Bek et al. |
| 2019/0274700 A1 | 9/2019 | Robertson et al. |
| 2020/0093507 A1 | 3/2020 | James et al. |
| 2020/0222237 A1 | 7/2020 | Urich et al. |

FOREIGN PATENT DOCUMENTS

| | | |
|---|---|---|
| EP | 3243467 A1 | 11/2017 |
| EP | 2533704 B1 | 10/2019 |
| JP | H0489042 A | 3/1992 |
| JP | 2002153500 A | 5/2002 |
| WO | 9501754 A1 | 1/1995 |
| WO | 9955240 A1 | 11/1999 |
| WO | 2009088390 A1 | 7/2009 |
| WO | 2020068756 A1 | 4/2020 |

OTHER PUBLICATIONS

English language abstract for JP 2002-153500 A extracted from espacenet.com database on Oct. 19, 2023, 2 pages.
International Search Report for Application No. PCT/IB2020/050314 dated Apr. 2, 2020, 4 pages.
Misonix, Inc., "SonaStar Laparoscopic Probe MXA-L002 Webpage", https://misonix.com/wp-content/uploads/2016/02/00400-SonaStar-LaproProbe-Revise_2.pdf, 2016, 2 pages.
TE Connectivity, "Heat Shrink Tubing MT 2000.6.0-0-SP Datasheet", https://www.te.com/usa-en/product-8876994002.html#guest-click, 2019, 4 pages.

* cited by examiner

ULTRASONIC SURGICAL IRRIGATION SLEEVE AND RELATED ASSEMBLIES

BACKGROUND

When using an ultrasonic instrument to cut tissue, the buildup of heat and biological debris can cause a variety of undesirable effects, such as damage to the ultrasonic instrument and/or surrounding tissue, and impaired visibility. To eliminate or reduce these undesirable effects, an irrigation and aspiration system may be used in tandem with the ultrasonic instrument. The irrigation and aspiration system usually involves irrigation fluid being conveyed alongside the ultrasonic instrument to a surgical site to irrigate the surgical site and to cool the ultrasonic instrument. A suction source can pull excess fluid and biological debris from the surgical site to provide better visibility.

Existing ultrasonic instruments may utilize a series of sleeves disposed over an ultrasonic tip of the ultrasonic instrument to guide the irrigation fluid and a central aspiration passage for suction. Such ultrasonic instruments, however, may be difficult to maneuver to certain surgical sites and/or may allow hot spots to occur along the ultrasonic tip. Preventing leakage of the irrigation fluid may also be difficult. Accordingly, there remains a need in the art to address one or more of these challenges.

SUMMARY

An ultrasonic surgical assembly includes an ultrasonic instrument having a proximal end and a distal end, and an aspiration passageway. The ultrasonic instrument also comprises a housing having a proximal portion and a distal portion, a transducer at least partially disposed within the housing, a horn coupled to the transducer, and an ultrasonic tip comprising a shaft coupled to the horn. The ultrasonic surgical assembly further comprises an irrigation sleeve assembly. The irrigation sleeve assembly comprises a hub releasably coupled to the distal portion of the housing and an irrigation sleeve coupled to the hub. The irrigation sleeve comprises an inner sheath extending distally from the hub. The inner sheath has a proximal end and an opposing distal end, and defines a lumen, which at least partially surrounds the shaft of the ultrasonic tip. An outer sheath extends distally from the hub. The outer sheath has a proximal end and an opposing distal end. The outer sheath surrounds a portion of the inner sheath to define an irrigation passageway between the outer sheath and the inner sheath. The distal end of the inner sheath extends beyond the distal end of the outer sheath. The irrigation passageway is configured to deliver irrigation fluid to a surgical site.

A tool assembly comprises an ultrasonic tip including a shaft, wherein the shaft defines an aspiration passageway. The tool assembly also comprises an irrigation sleeve assembly. The irrigation sleeve assembly comprises a hub and an irrigation sleeve coupled to the hub. The irrigation sleeve comprises an inner sheath extending distally from the hub. The inner sheath has a proximal end and an opposing distal end. The inner sheath defines a lumen, which at least partially surrounds the shaft of the ultrasonic tip. An outer sheath extends distally from the hub. The outer sheath has a proximal end and an opposing distal end. The outer sheath surrounds a portion of the inner sheath to define an irrigation passageway, between the outer sheath and the inner sheath. The distal end of the inner sheath extends beyond the distal end of the outer sheath. The irrigation passageway is configured to deliver irrigation fluid to a surgical site.

An irrigation sleeve assembly is used with an ultrasonic tip of an ultrasonic instrument. The irrigation sleeve assembly comprises a hub configured to be releasably coupled to the ultrasonic instrument. The irrigation sleeve assembly also comprises an irrigation sleeve coupled to the hub. The irrigation sleeve comprises an inner sheath extending distally from the hub. The inner sheath has a proximal end and an opposing distal end. The inner sheath defines a lumen configured to at least partially surround the ultrasonic tip. An outer sheath extends distally from the hub. The outer sheath has a proximal end and an opposing distal end. The outer sheath is configured to surround a portion of the inner sheath and define an irrigation passageway between the outer sheath and the inner sheath. The irrigation passageway is configured to deliver irrigation fluid to a surgical site. An annular sealing member surrounds at least a portion of the hub and the outer sheath. The annular sealing member is configured to prevent egress of fluid from the hub and outer sheath.

These and other examples, configurations, features, and advantages of the present disclosure will be apparent to those skilled in the art. The present disclosure is not to be limited to or by these examples, configurations, features, and advantages.

BRIEF DESCRIPTION OF THE DRAWINGS

Advantages of the present disclosure will be readily appreciated, as the same becomes better understood by reference to the following detailed description when considered in connection with the accompanying drawings.

DETAILED DESCRIPTION

Figure 1:
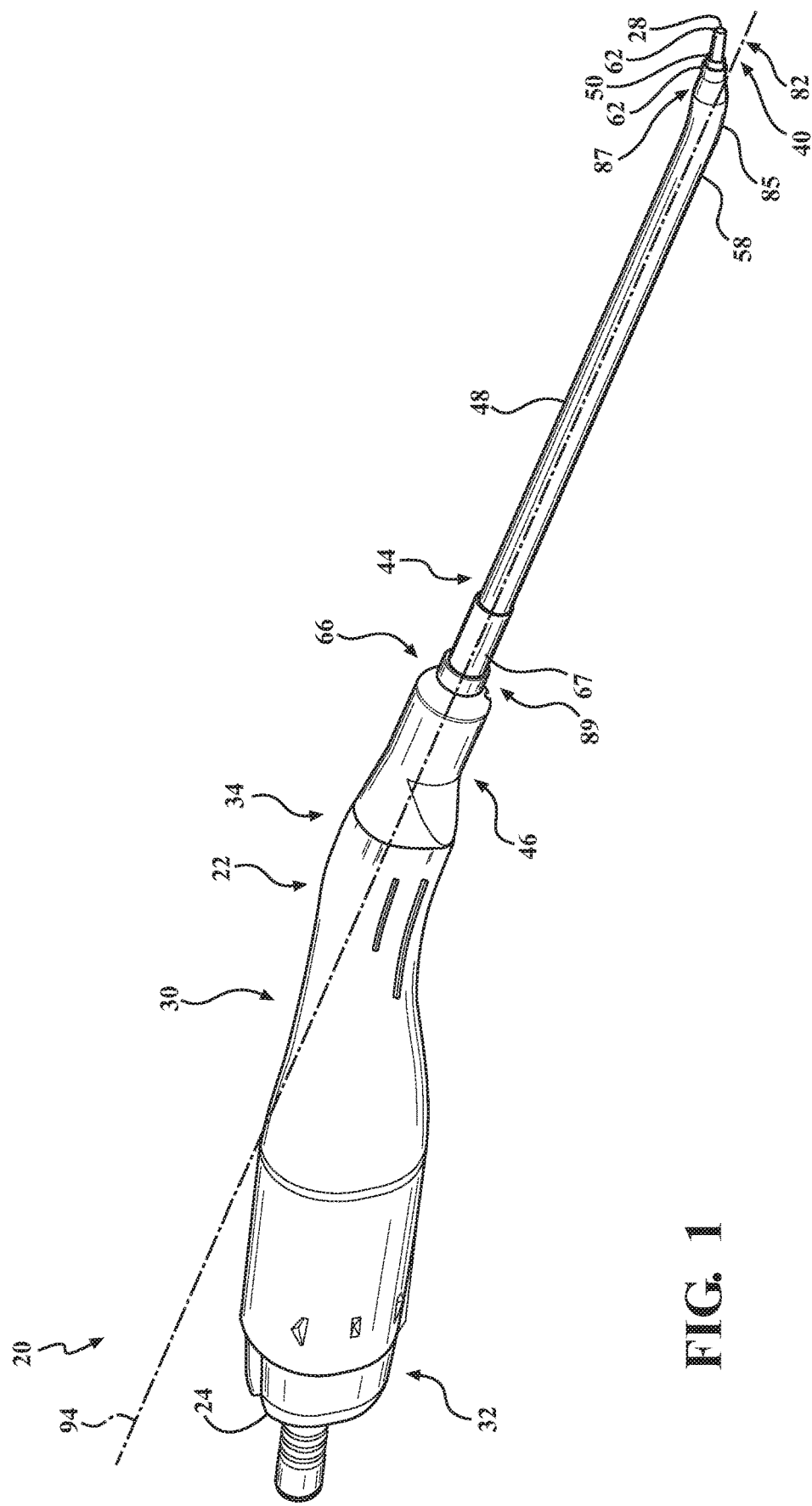
FIG. 1 is a perspective view of an ultrasonic surgical assembly.
Figure 2:
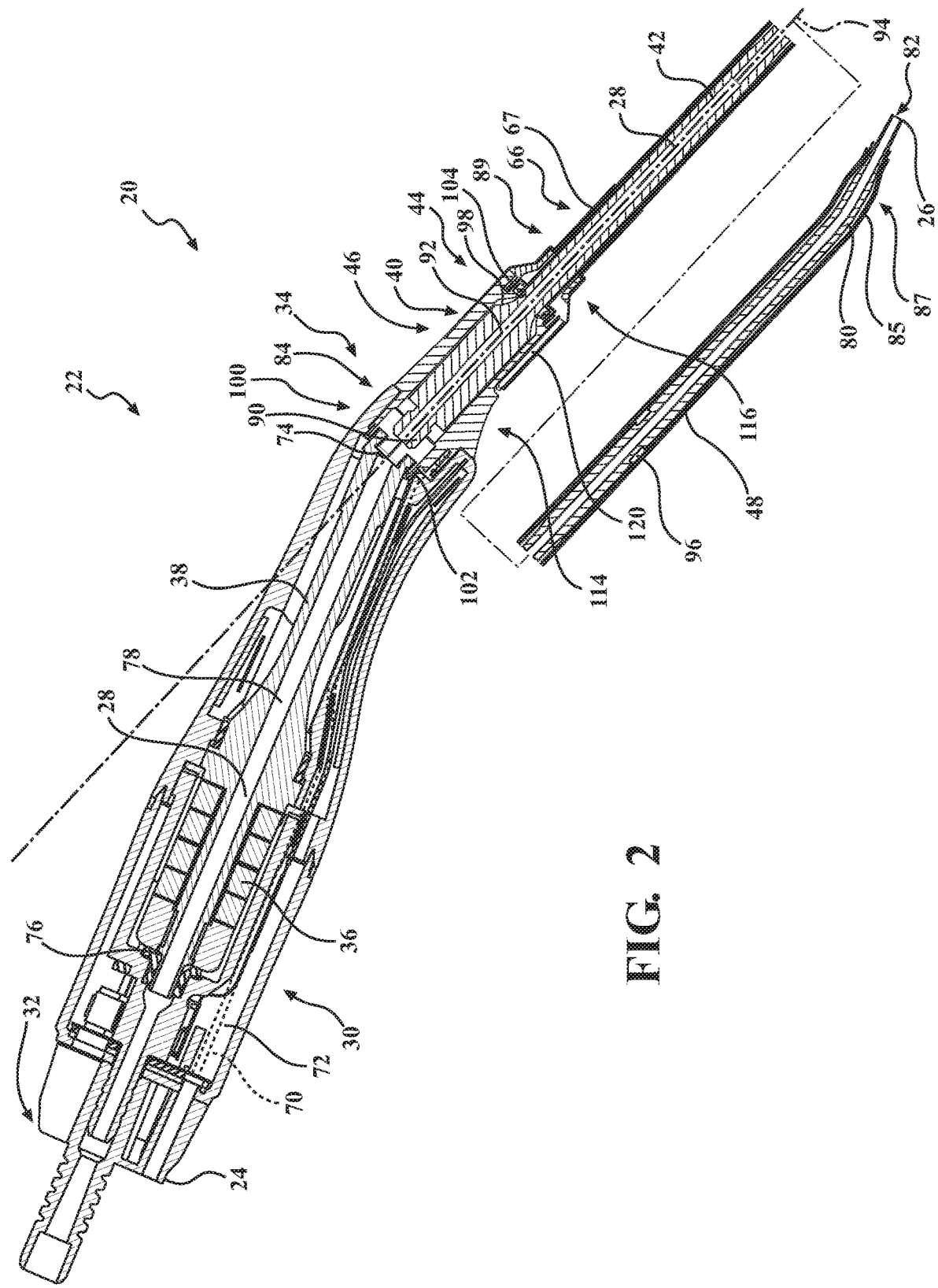
FIG. 2 is a sectional view of the ultrasonic surgical assembly.

FIGS. 1 and 2 illustrate an ultrasonic surgical assembly 20 that may be utilized by a user, such as a surgeon, to remove/cut biological material from a patient. The ultrasonic surgical assembly 20 comprises an ultrasonic instrument 22 having a proximal end 24, a distal end 26, and an aspiration passageway 28. The ultrasonic instrument 22 comprises a housing 30 including a proximal portion 32 and a distal portion 34, a transducer 36 at least partially disposed within the housing 30 (see FIG. 2), a horn 38 coupled to the transducer 36, and an ultrasonic tip 40 to remove/cut the biological material from the patient.

Referring to FIG. 2, the transducer 36 is at least partially disposed within the housing 30. The transducer 36 may comprise one or more piezoelectric elements, magnetostrictive elements, or other suitable elements configured to generate mechanical energy to be provided to the horn 38 and ultimately transmitted through the ultrasonic tip 40 to the surgical site.

The horn 38 may be at least partially disposed within the housing 30. The horn 38 may comprise a distal end 74 and a proximal end 76. The horn 38 is coupled to the transducer 36. The horn 38 may also be configured to define a horn lumen 78 that extends from the distal end 74 to the proximal end 76 of the horn 38. The horn lumen 78 may define a portion of the aspiration passageway 28.

The ultrasonic tip 40 may comprise a shaft 42 that has a distal portion 82 and a proximal portion 84. The ultrasonic tip 40 may also comprise a coupling feature 90 positioned at the proximal portion 84 of the shaft 42 to couple the proximal portion 84 of the shaft 42 to the distal end 74 of the horn 38 so that the horn 38 is in mechanical communication with the ultrasonic tip 40. The coupling feature 90 may be a threaded coupler configured to engage a corresponding threaded coupler on the distal end 74 of the horn 38. The ultrasonic tip 40 may be threaded into the horn 38 and tightened to a predetermined torque specification to removably secure the ultrasonic tip 40 to the horn 38. While not illustrated in the figures, it is contemplated that the coupling feature 90 may be configured as a quick connection, quarter-turn fitting, or similar coupling mechanism. It is further contemplated that the coupling feature 90 may be configured to permanently affix the ultrasonic tip 40 to the horn 38. For example, the ultrasonic tip 40 may be coupled to the horn 38 by a weld, epoxy, or similar method. Alternatively, it is also contemplated that the ultrasonic tip 40 and the horn 38 may be formed as a unitary component.

The shaft 42 of the ultrasonic tip 40 may also be configured to define a shaft lumen 92 that extends from the proximal portion 84 to the distal portion 82. The shaft lumen 92 may be oriented to be generally parallel to a longitudinal axis 94, but may be formed in other shapes. The shaft lumen 92 of the ultrasonic tip 40 may be optionally configured to define a portion of the aspiration passageway 28 in communication with the horn lumen 78, when the ultrasonic tip 40 is coupled to the horn 38. The aspiration passageway 28 may be open at the distal portion 82 of the shaft 42. The aspiration passageway 28 may be configured to provide aspiration away from the surgical site. For example, the aspiration passageway 28 may be used to draw fluid and biological tissue away from the distal portion 82 of the ultrasonic tip 40.

The shaft 42 may be made of a metal material such as titanium alloy, stainless steel, etc., a non-metallic material such as a composite, combinations thereof, and the like, depending on the application. Other suitable materials are also contemplated. The ultrasonic tip 40 may be integral, unitary, and one-piece, but could be formed of multiple components. It should be appreciated that the diameter of the distal portion 82 of the shaft 42 may be a relatively small diameter, for example less than one centimeter (1 cm), so as to work in a small opening of the patient. It should further be appreciated that the shaft 42 may be scaled larger or smaller depending on the application.

Figure 3:
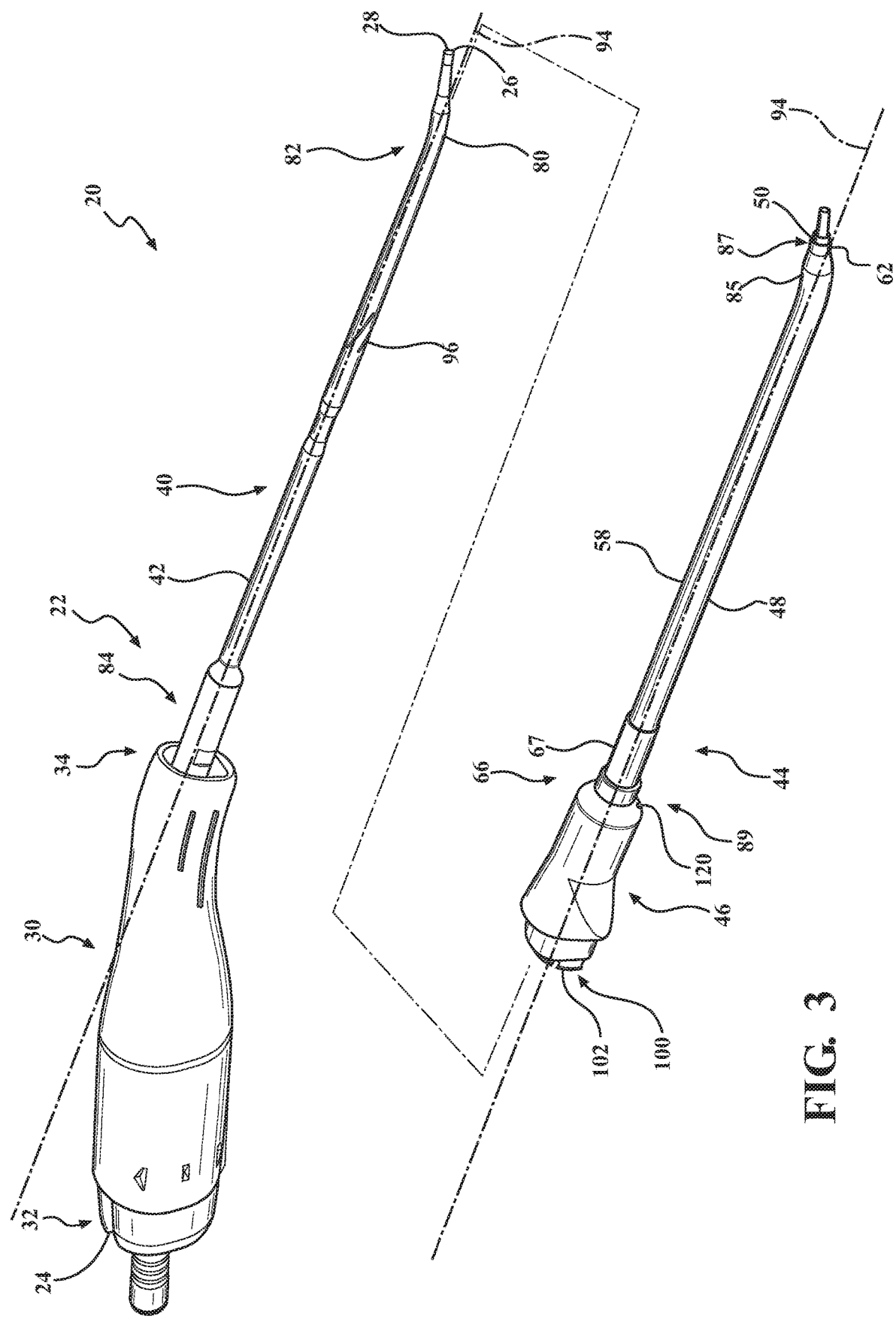
FIG. 3 is a partially exploded perspective view of an ultrasonic instrument and an irrigation sleeve assembly.
Figure 4:
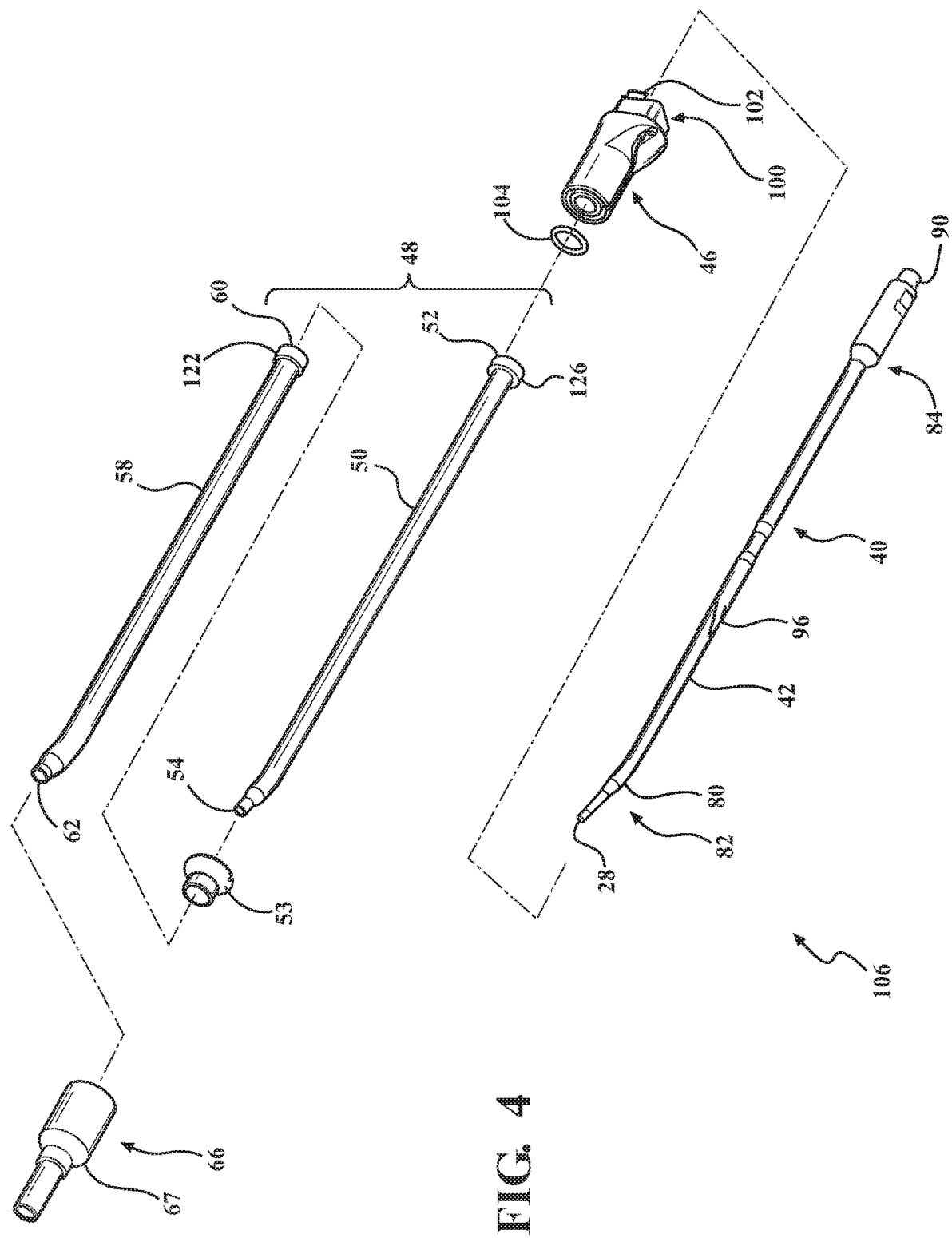
FIG. 4 is an exploded view of the irrigation sleeve assembly, an ultrasonic tip, and an annular sealing member.

Referring to FIGS. 2, 3, and 4, the ultrasonic tip 40 may further comprise a vibration conversion mechanism 96 for converting a vibration energy transmitted from the transducer 36 into a composite vibration composed of a longitudinal vibration and a torsional vibration. Details regarding the vibration conversion mechanism 96 may be found in U.S. Pat. Nos. 6,497,715; 6,955,680; and 6,984,220; which are hereby incorporated herein by reference in their entirety.

The ultrasonic tip 40 allows the efficient removal of biological tissue with torsional and/or longitudinal motion of the ultrasonic tip 40. However, it should be appreciated that the ultrasonic tip 40 may also be used with transducers 36 that vibrate longitudinally, torsionally, combinations thereof, or that vibrate in other ways. Furthermore, in some configurations, the vibration conversion mechanism 96 is absent.

The ultrasonic tip 40 may have a bend 80 wherein the distal portion 82 of the ultrasonic tip 40 bends relative to the proximal portion 84 of the ultrasonic tip 40. The bend 80 of the ultrasonic tip 40 may be configured to allow better line of sight while using the ultrasonic surgical assembly 20. Additionally, in some surgical procedures, the bend 80 enables easier access to the surgical site within the patient. The ultrasonic tip 40 may have a single bend 80 as shown, multiple bends, no bends, or the like. Other shapes of the ultrasonic tip 40 are also contemplated.

As shown in FIG. 2, the housing 30 may comprise an irrigation line 70 disposed within a housing void 72, or routed external to the housing 30. The irrigation line 70 may be configured to extend from the proximal portion 32 of the housing 30 to the distal portion 34 of the housing 30. The irrigation line 70 may serve to channel fluid from an irrigation system that is coupled to the ultrasonic instrument 22 through the housing 30 to an irrigation sleeve assembly 44. It should be appreciated that the irrigation line 70 may route directly from an irrigation source (not shown) to the irrigation sleeve assembly 44 (i.e., the irrigation line need not be always routed through the housing 30).

Referring to FIGS. 2-5 and 10, the irrigation sleeve assembly 44 comprises a hub 46 releasably coupled to the distal portion 34 of the housing 30 and an irrigation sleeve 48 coupled to the hub 46. The hub 46 may comprise a hub coupling mechanism 100. The hub coupling mechanism 100 may comprise one or more fingers 102 extending proximally from a main body of the hub 46. Each of the one or more fingers 102 may comprise a tab extending in a radially outward direction relative to the longitudinal axis 94 when assembled onto the ultrasonic instrument 22. The fingers 102 act as male fittings/features configured to couple with female fittings/features on the distal portion 34 of the housing 30 to create a snap-fit, interference fit, or other suitable connection. It is contemplated that other types of hub coupling mechanisms 100 may be used to couple the irrigation sleeve assembly 44 to the housing 30. For example, the hub coupling mechanism 100 may be configured as a threaded connection. An exemplary configuration of an ultrasonic instrument and irrigation sleeve is described in U.S. application Ser. No. 16/580,639 and PCT/US2019/052609 owned by Applicant, both of which are incorporated herein by reference in their entirety.

The hub 46 may define a hub lumen 98 (see FIG. 5) configured to at least partially house a portion of the shaft 42 of the ultrasonic tip 40 when the irrigation sleeve assembly 44 is coupled to the housing 30. A combination of the irrigation sleeve assembly 44 and the ultrasonic tip 40 may be referred to as a tool assembly 106.

As best shown in FIGS. 4-9, the irrigation sleeve 48 may comprise an inner sheath 50 extending distally from the hub 46. The inner sheath 50 has a proximal end 52 and an opposing distal end 54. The inner sheath 50 defines a lumen 56, which at least partially surrounds the shaft 42 of the ultrasonic tip 40. The irrigation sleeve 48 may also comprise an outer sheath 58 extending distally from the hub 46. The outer sheath 58 has a proximal end 60 and an opposing distal end 62. The size of the outer diameter of the outer sheath 58 is not intended to be limited, however, it is contemplated that for minimally invasive or keyhole type surgeries, the irrigation sleeve 48 may comprise an outer sheath 58 having an outer diameter of ten (10) millimeters (mm) or less. Furthermore, for some medical procedures the outer sheath 58 may be configured to have an outer diameter of seven (7) millimeters (mm) or less. This allows the sleeve to be used in minimally invasive and keyhole surgeries.

The outer sheath 58 surrounds a portion of the inner sheath 50 to define an irrigation passageway 64 between the outer sheath 58 and the inner sheath 50. The irrigation passageway 64 is configured to deliver irrigation fluid to the surgical site (not shown). The inner sheath 50 and the outer sheath 58 form an annular gap 108 there between to define the irrigation passageway 64, best seen in FIGS. 6-9. The annular gap 108 of the irrigation passageway 64 allows for the diameter of the irrigation sleeve 48 to be relatively small. The small diameter allows the user to access difficult to reach anatomical areas and enter through smaller access portals, which may result in quicker recovery times. The outer sheath 58 may be configured to move independently of the inner sheath 50 to maintain the irrigation passageway 64 between the inner sheath 50 and the outer sheath 58. The inner and outer sheaths 50, 58 may each optionally comprise a flexible material. In certain configurations, one of the outer sheath 58 or the inner sheath 50 may be omitted and only a single sheath may be utilized.

The irrigation sleeve 48 may be more flexible than the ultrasonic tip 40 for positioning the irrigation sleeve 48 over the ultrasonic tip 40. The irrigation sleeve assembly 44 may be configured to slide over the ultrasonic tip 40 to couple the irrigation sleeve assembly 44 to the housing 30 while still maintaining the lumen 56. The lumen 56 of the inner sheath 50 may be sized to define a gap 110 between the inner sheath 50 and the ultrasonic tip 40. For example, if the user was performing a nasal surgery with the ultrasonic instrument 22, the user may attempt to gain access to the surgical site through a patient's nasal cavity. The irrigation sleeve 48 may experience a force in the inward radial direction from the patient's nasal cavity. The outer sheath 58 may pinch while the inner sheath 50 may maintain the gap 110 uniformly between the inner sheath 50 and the ultrasonic tip 40. Additionally, the inner sheath 50 may continue to define the lumen 56 that surrounds the shaft 42 of the ultrasonic tip 40, while the outer sheath 58 experiences the inward radial force. Accordingly, the inner sheath 50 may be configured to be more flexible than the outer sheath 58 in some examples, but it is also contemplated that the inner sheath 50 may comprise the same flexibility, or may be configured to be less flexible than the outer sheath 58 in other exemplary configurations. When the user is attempting to reach the surgical site within the patient, the irrigation sleeve 48 may become temporarily pinched. The outer sheath 58 may temporarily bend or deform towards the inner sheath 50. The region of the irrigation sleeve 48 that is pinched may have a raised temperature because of the lack of irrigation fluid flowing in the region. Once the pinch is released, the resilient nature of the inner sheath 50 and/or outer sheath 58 may spring back to the shape before the pinch, owing to its resilient nature, allowing fluid to again flow causing the temperature to decrease. Because of the flexibility of the inner and outer sheaths 50, 58, a pinch will locally squeeze the inner and outer sheaths 50,58 so that they touch each other but there will still be a lumen allowing the fluid to travel to the surgical site proximate the distal end of ultrasonic tip 40. The pinch point may get hot as the inner sheath 50 rubs against the vibrating ultrasonic tip 40 without local cooling flowing to the pinched region of the irrigation sleeve 48.

The irrigation sleeve assembly 44 may comprise a polymer, for example a thermoplastic, or any other suitable materials, such as plastics, combinations thereof, and the like. The hub 46 and the irrigation sleeve 48 may comprise one or more different species of polymers or other materials. In some configurations, the hub 46 may be formed from thermoplastic, synthetic polymer, polyoxymethylene (Delrin®, POM, acetal, polyacetal, polyformaldehyde), polyether ether ketone (PEEK), metal, aluminum, steel, titanium, other suitable materials, and combinations thereof. In some configurations, the inner sheath 50 and the outer sheath 58 of the irrigation sleeve 48 may be formed from perfluoroalkoxy alkane (PFA), polytetrafluoroethylene (PTFE), other suitable synthetic fluoropolymers, heat shrink material such as polyolefin, other suitable materials, and combinations thereof.

Figure 5:
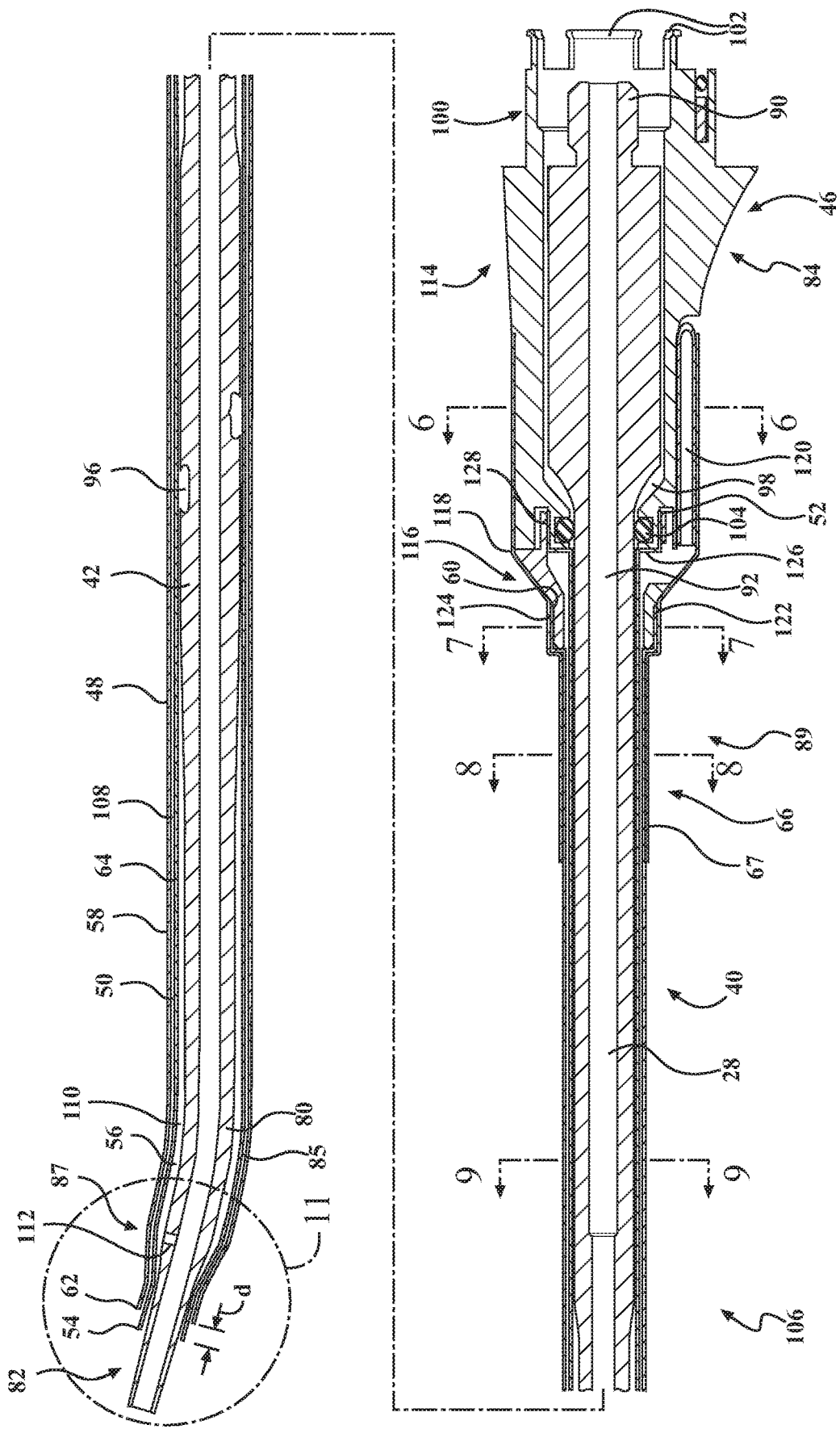
FIG. 5 is a sectional view of the irrigation sleeve assembly, the ultrasonic tip, and the annular sealing member.
Figure 7:
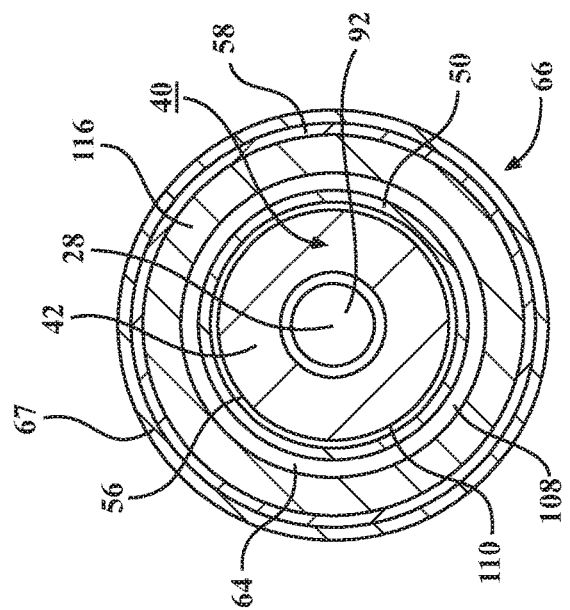
FIG. 7 is a sectional view of FIG. 5 taken along line 7-7.
Figure 9:
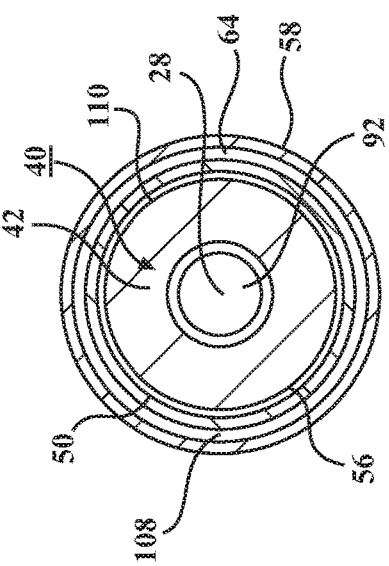
FIG. 9 is a sectional view of FIG. 5 taken along line 9-9.

Referring to FIG. 5, the distal end 54 of the inner sheath 50 may extend beyond the distal end 62 of the outer sheath 58 by a distance (d). The inner sheath 50 may be longer than the outer sheath 58, at their distal ends 54, 62, to keep the shaft 42 of the ultrasonic tip 40, proximal of the distal end 54 of the inner sheath 50, relatively dry and free from irrigation fluid. The distance (d) may prevent irrigation fluid from the irrigation passageway 64 entering the gap 110 between the inner sheath 50 and the ultrasonic tip 40. Irrigation fluid flowing and pooling in the gap 110 between the inner sheath 50 and the ultrasonic tip 40 may cause the irrigation fluid to overheat and could otherwise damage the ultrasonic surgical assembly 20.

There is also a concern regarding elevation of temperature. This is a typical challenge in endonasal procedures as the surgeon may not be aware of the temperature of the irrigation sleeve 48. While not illustrated in the Figures, it is also contemplated that the inner sheath 50 may be configured such that the distal end 54 on the inner sheath is positioned even with the distal end 62 of the outer sheath 58. Furthermore, it is contemplated that the inner sheath 50 may be configured such that the distal end 54 on the inner sheath is positioned proximally to the distal end 62 of the outer sheath 58. The specific arrangement of the position of the distal end 54 of the inner sheath 50 relative to the distal end 62 of the outer sheath 58 may be configured based on the preferred flow pattern and/or spray direction of the fluid relative to the distal portion 82 of the ultrasonic tip and/or the surgical site.

In some examples, the irrigation sleeve 48 has a sleeve bend 85 corresponding to the bend 80 on the ultrasonic tip 40 to allow the irrigation sleeve 48 to partially surround the ultrasonic tip 40. The irrigation sleeve 48 may be flexible and have a distal portion 87 and an opposing proximal portion 89, wherein the distal portion 87 of the irrigation sleeve 48 may be configured to bend relative to the proximal portion 89 of the irrigation sleeve 48 to form the sleeve bend 85 when disposing the irrigation sleeve 48 over the ultrasonic tip 40. The sleeve bend 85 may also be a preformed shape of the irrigation sleeve 48. In some examples, the irrigation sleeve 48 has additional bends, no bends, and/or may be formed in other shapes.

As best shown in FIGS. 4 and 5, an annular sealing member 66 is configured to prevent egress of fluid from the hub 46. The annular sealing member 66 may be configured to be circumferentially disposed about the hub 46, inner sheath 50, outer sheath 58, combinations thereof, or other suitable arrangements. For example, the annular sealing member 66 may be configured to couple the outer sheath 58 to the hub 46 and/or create a fluid-tight between the joint formed between the outer sheath 58 and hub 46. The annular sealing member 66 may be press fit onto hub 46, may be welded to the hub 46, may be threadably coupled to the hub 46, and/or may be coupled to the hub 46 using other acceptable fastening techniques. It is also contemplated that the hub 46 may comprise grooves, recess, barbs, threads, or other similar features to assist in coupling the outer sheath 58 to the hub 46. For example, the hub 46 may comprise an annular groove in an exterior surface configured to create a snap or press-fit with an interior surface of the outer sheath 58 as when it is coupled to the hub 46. In one configuration, the annular sealing member 66 is positioned on the periphery of the hub 46 and the outer sheath 58. In another configuration, the annular sealing member is positioned to radially surround at least a portion of each of the outer surfaces of the hub 46 and outer sheath 58. The annular sealing member 66 may comprise a polymer, an elastomer, or combinations thereof. The annular sealing member 66 may comprise a sealing sleeve 67. The annular sealing member may comprise a heat shrink material that may be positioned over the joint formed between the outer sheath 58 and the hub 46 such that at least a portion of the annular sealing member 66 is disposed over the outer sheath 58 and the hub 46. The annular sealing member 66 may be configures such that when a heat source is applied to the heat shrink material, the annular sealing member shrinks around the outer sheath 58 and hub 46 coupling the outer sheath 58 to the hub 46 and forming a fluid-tight seal at the joint. The heat shrink material may comprise fluoropolymers, cross-linked fluoropolymers, cross-linked polyether block amide (PEBA) with polyolefin, medical grade polyolefin, cross-linked acrylated olefin, polyvinylidene fluoride, polyvinylidene difluoride (PVDF), high-density polyethylene (HDPE), low-density polyethylene (LDPE), polyvinyl chloride (PVC), Viton®, Neoprene®, Kynar®, polytetrafluoroethylene (PTFE), polyethylene terephthalate (PET), fluorinated ethylene propylene (FEP), combinations thereof, and/or other suitable sealing materials.

Figure 10:
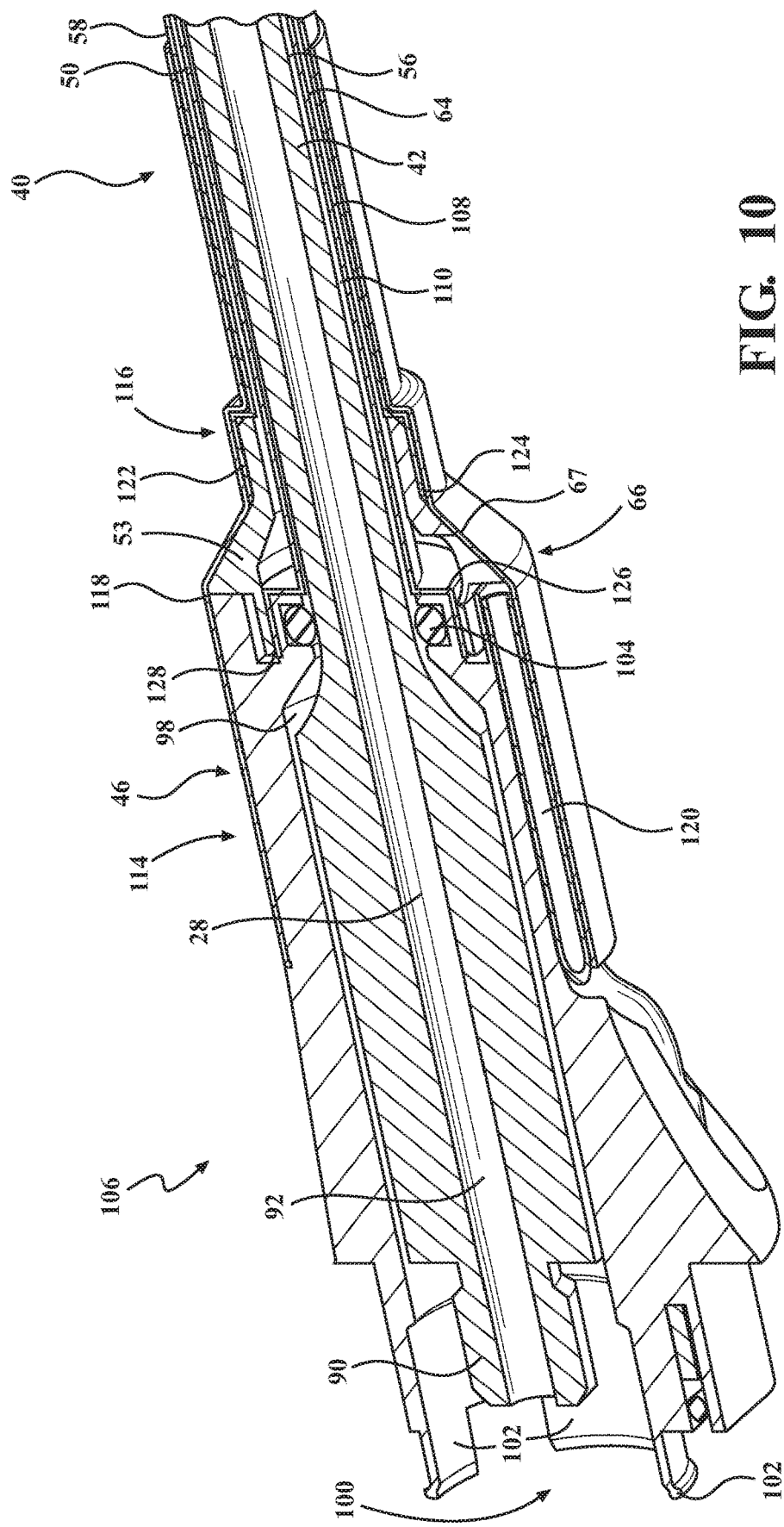
FIG. 10 is a detailed perspective and sectional view of the irrigation sleeve assembly, the ultrasonic tip, and the annular sealing member.

As shown in FIGS. 4, 5, and 10, the irrigation sleeve assembly 44 may further comprise an inner seal 104 disposed within the hub 46 to assist with creating a seal between the ultrasonic tip 40 and the hub 46. For example, as illustrated in FIGS. 4 and 5, the inner seal 104 comprises an O-ring disposed within a recess in the hub 46. The inner seal 104 may be disposed within the hub 46 and circumferentially around the shaft 42 of the ultrasonic tip 40. The inner seal 104 may be configured to prevent irrigation fluid and/or biological material that may get between the inner sheath 50 and the ultrasonic tip 40 from entering the housing 30 of the ultrasonic instrument 22 between the exterior surface of the ultrasonic trip and the interior surface of the inner sheath 50. The inner seal 104 may comprise one or more polymer, elastomer, fluoroelastomer (FKM), ethylene propylene, ethylene propylene diene monomer (EPDM), medical grade silicone, nitrile, combinations thereof, or any other suitable sealing materials.

Figure 6:
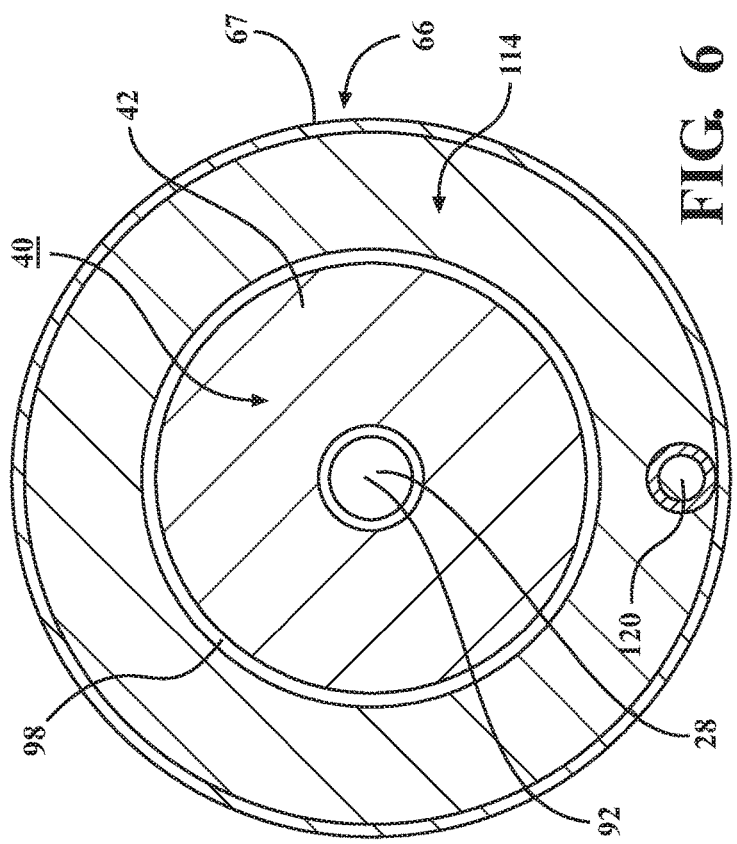
FIG. 6 is a sectional view of FIG. 5 taken along line 6-6.
Figure 8:
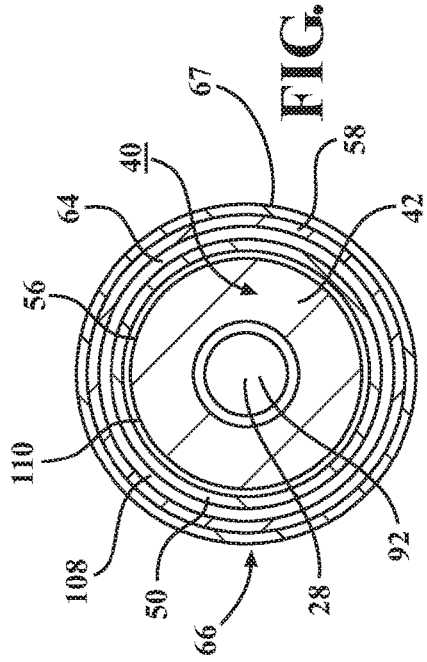
FIG. 8 is a sectional view of FIG. 5 taken along line 8-8.

Referring to FIGS. 5 and 10, the hub 46 comprises a first hub portion 114 and a second hub portion 116 connected to the first hub portion 114 to define a hub joint 118. The first hub portion 114 may be connected to the second hub portion 116 by welding, interference fit, snap-fit, or any other suitable connecting method. The first hub portion 114 may comprise an irrigation conduit 120 configured to deliver fluid from the irrigation line 70 to the irrigation passageway 64 defined between the inner and outer sheaths 50, 58. The irrigation passageway 64 of the irrigation sleeve 48 is formed by the arrangement of the inner and outer sheaths 50, 58 relative to the hub 46, such that the irrigation sleeve 48 does not require a specific fitting or conduit to couple with the irrigation conduit 120. As illustrated in FIG. 6, the distal opening of the irrigation conduit 120 is positioned within the gap between the inner and outer sheaths 50, 58 and configured to spray and/or disperse fluid directly into the irrigation passageway 64 without need for a specific attachment mechanism or coupler to connect the irrigation conduit 120 to the irrigation passageway 64. Thus, the irrigation line 70 may be in fluid communication with the irrigation conduit 120 via any suitable fluid connection. In some examples, the irrigation line may be configured to be disposed in a proximal end of the irrigation conduit 120 so that the irrigation fluid is able to be routed through the hub 46 to the irrigation passageway 64 (see FIG. 10).

The irrigation fluid may be introduced into the irrigation passageway 64 between the inner sheath 50 and outer sheath 58. The fluid flowing from the irrigation conduit 120 to the irrigation passageway 64 may result in fluid resistance and associated forces acting between the first and second hub portions 114, 116. Accordingly, the sealing sleeve 67 may at least partially surround the first hub portion 114 and the second hub portion 116 at the hub joint 118 to seal the hub joint 118. The sealing sleeve 67 may provide structural strength to sealably secure the first hub portion 114 to the second hub portion 116.

In some examples, the sealing sleeve 67 further provides rigidity to the irrigation sleeve 48. The sealing sleeve 67 allows the user to have a location to grip the irrigation sleeve assembly 44. The sealing sleeve 67 may be utilized to prevent kinking of the irrigation sleeve 48 when removing the irrigation sleeve assembly 44 from packaging. Additionally, the user may grip the sealing sleeve 67 to remove the irrigation sleeve assembly 44 from the ultrasonic instrument 22. For example, the sealing sleeve 67 may provide a barrier between the user and the irrigation sleeve 48.

As shown in FIGS. 5 and 10, the outer sheath 58 may comprise an outer sheath flange 122 engaging an annular collar of the second hub portion 116 to define an outer sheath joint 124. The outer sheath flange 122 may be press fit onto the annular collar of the second hub portion 116, may be welded to the annular collar, and/or may be coupled to the second hub portion 116 in other ways. The outer sheath flange 122 may be cylindrical in shape and/or may comprise other shapes to engage the second hub portion 116. The annular sealing member 66 at least partially surrounds the second hub portion 116 and the outer sheath 58 at the outer sheath joint 124 to seal the outer sheath joint 124. Similar to the hub joint 118, the outer sheath joint 124 may experience fluid resistance and associated forces acting between the second hub portion 116 and the outer sheath flange 122. The sealing sleeve 67 provides strength to sealably secure the outer sheath 58 to the second hub portion 116.

The inner sheath 50 may define an inner sheath flange 126 engaging an annular collar of the first hub portion 114 to define an inner sheath joint 128. The inner sheath flange 126 may be press fit onto the annular collar of the first hub portion 114, may be welded to the annular collar, and/or may be coupled to the first hub portion 114 in other ways. For example, the inner sheath flange 126 may be coupled to the first hub portion 114 by a second annular sealing member 53. The second annular sealing member 53 may be configured to at least partially encircle the inner sheath flange 126 of the inner sheath and be press fit in the annular collar of the first hub portion 114 to define the inner sheath joint 128. It is also contemplated that the second annular sealing member 53 may be coupled to the first hub 114 portion by a weld, an epoxy, or a similar adhesive. It is also contemplated that the second annular sealing member 53 may configured to threadably couple the inner sheath 50 to the hub. The hub 46 may comprise grooves, recess, barbs, threads, or other similar features to assist in coupling the inner sheath 50 to the hub 46. For example, the hub 46 may comprise an annular groove in an exterior surface configured to create a snap or press-fit with an interior surface of the inner sheath 50 as when it is coupled to the hub 46. It is further contemplated that the second annular sealing member 53 may comprise a heat shrink material configured to be disposed over the inner sheath flange 126 and heat treated to couple the inner sheath 50 to the hub 46. The inner sheath flange 126 may be cylindrical in shape and/or may comprise other shapes to engage the first hub portion 114. The inner sheath joint 128 may be at least partially surrounded by the annular sealing member 66. The inner sheath flange 126 may be radially captured between the first hub portion 114 and the second hub portion 116 to be sealed therebetween. The second annular sealing member 53 may comprise a heat shrink material that may be positioned over the inner sheath joint 128 formed between the inner sheath 50 and the hub 46 such that at least a portion of the second annular sealing member 53 is disposed over the inner sheath 50 and the hub 46. The second annular sealing member 53 may be configured such that when a heat source is applied to the heat shrink material, the second annular sealing member 53 shrinks around the inner sheath 50 and hub 46 coupling the inner sheath 50 to the hub 46 and forming a fluid-tight seal at the inner sheath joint 128. As described above, the hub 46 may comprise a groove or similar feature to facilitate coupling of and creation of the seal between hub 46 and the inner sheath. The heat shrink material may comprise fluoropolymers, cross-linked fluoropolymers, cross-linked polyether block amide (PEBA) with polyolefin, medical grade polyolefin, cross-linked acrylated olefin, polyvinylidene fluoride, polyvinylidene difluoride (PVDF), high-density polyethylene (HDPE), low-density polyethylene (LDPE), polyvinyl chloride (PVC), Viton®, Neoprene®, Kynar®, polytetrafluoroethylene (PTFE), polyethylene terephthalate (PET), fluorinated ethylene propylene (FEP), combinations thereof, and/or other suitable sealing materials.

In some examples, the irrigation passageway 64 may be configured to move fluid from the irrigation conduit 120 to the distal ends 54, 62 of the inner and outer sheaths 50, 58 by the utilization of capillary action. Capillary action, also known as capillarity, capillary motion, capillary effect, or wicking, may be the ability of a liquid to flow in narrow spaces without the assistance of, or even in opposition to, external forces like gravity. The capillary action of fluid through the irrigation passageway 64 may be advantageous because it can evenly distribute any heat generated by the ultrasonic tip 40 and prevent any buildup of heat that may result in damage to the ultrasonic surgical assembly 20.

Figure 11:
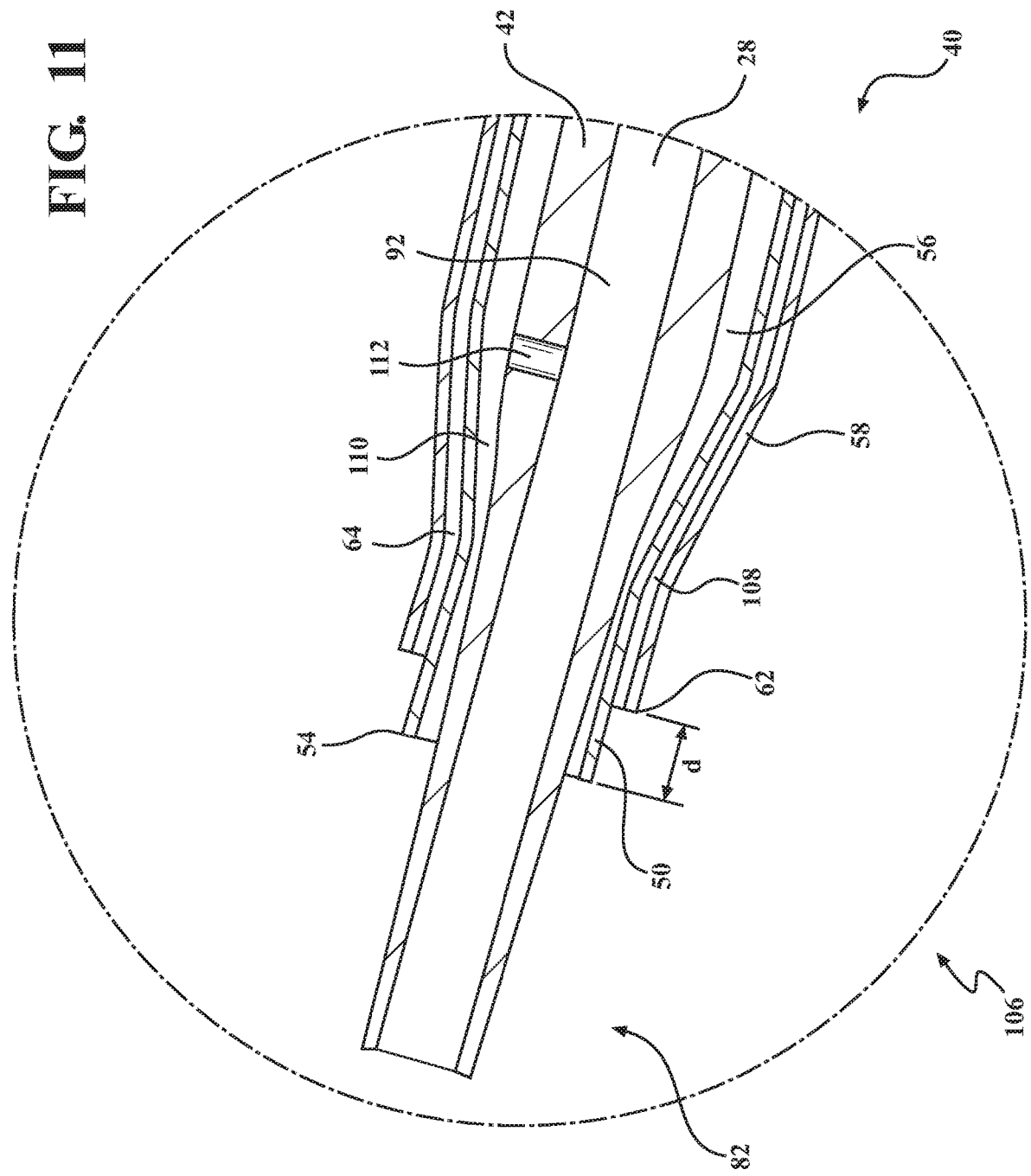
FIG. 11 is a detailed view of the irrigation sleeve assembly including the ultrasonic tip of FIG. 5 within circle 11.

The ultrasonic tip 40 may comprise an aperture 112 located in the shaft 42 and configured to be in fluid communication with the aspiration passageway 28, as shown in FIGS. 5 and 11. The aperture 112 may be located proximal to the distal end 54 of an inner sheath 50 and distal to the vibration conversion mechanism 96. The axis of the aperture 112 may be transverse to the aspiration passageway 28. In some configurations, the axis of the aperture 112 may be perpendicular to the aspiration passageway 28. The diameter of the aperture 112 may be smaller than the diameter of the aspiration passageway 28. The aperture 112 may prevent fluid from flowing between the ultrasonic tip 40 and the inner sheath 50 via suction of the fluid into the aspiration passageway 28. Additional apertures 112 may be present in some examples, and the aperture 112 may be absent in some examples.

Figure 12:
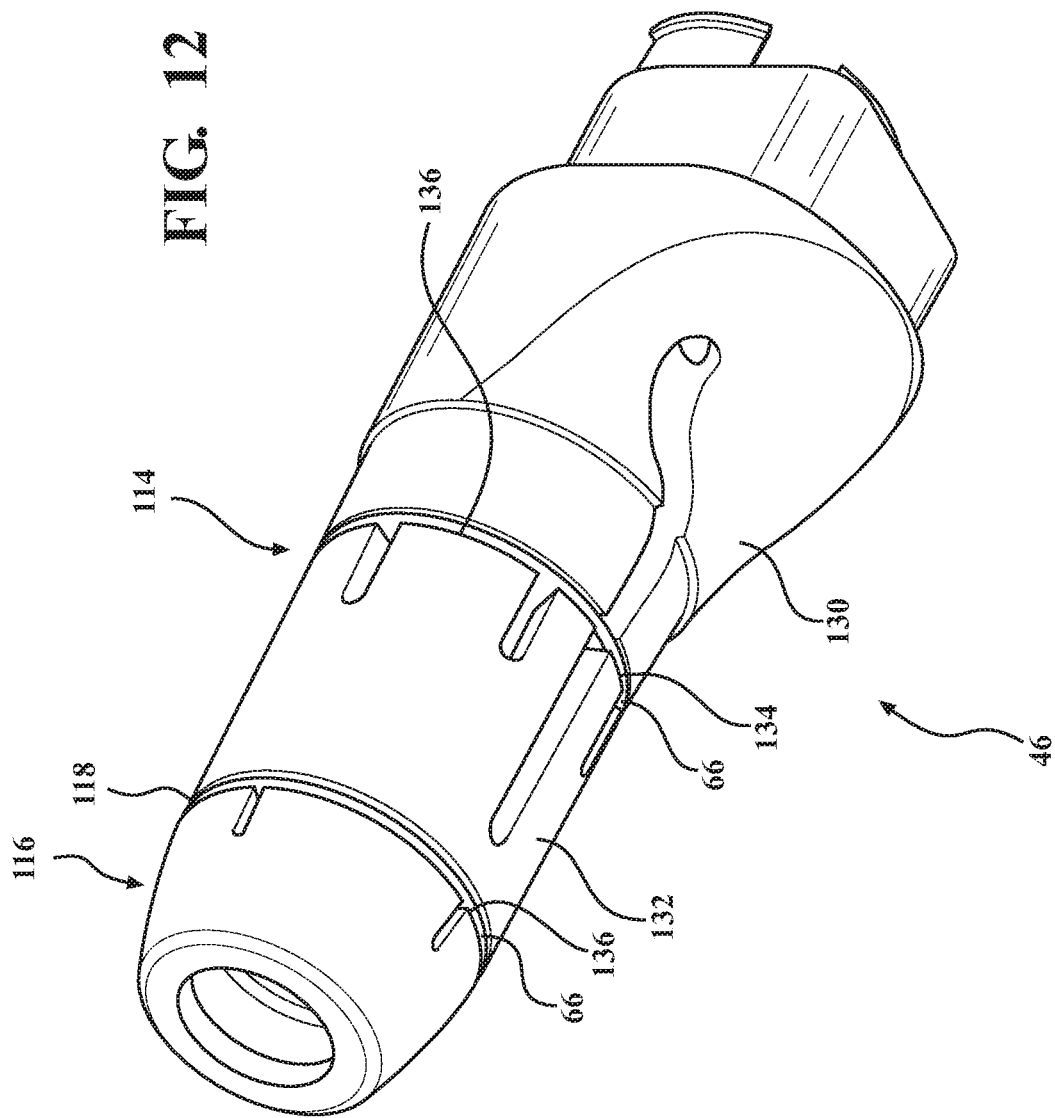
FIG. 12 is a perspective view of one configuration of a hub.
Figure 13:
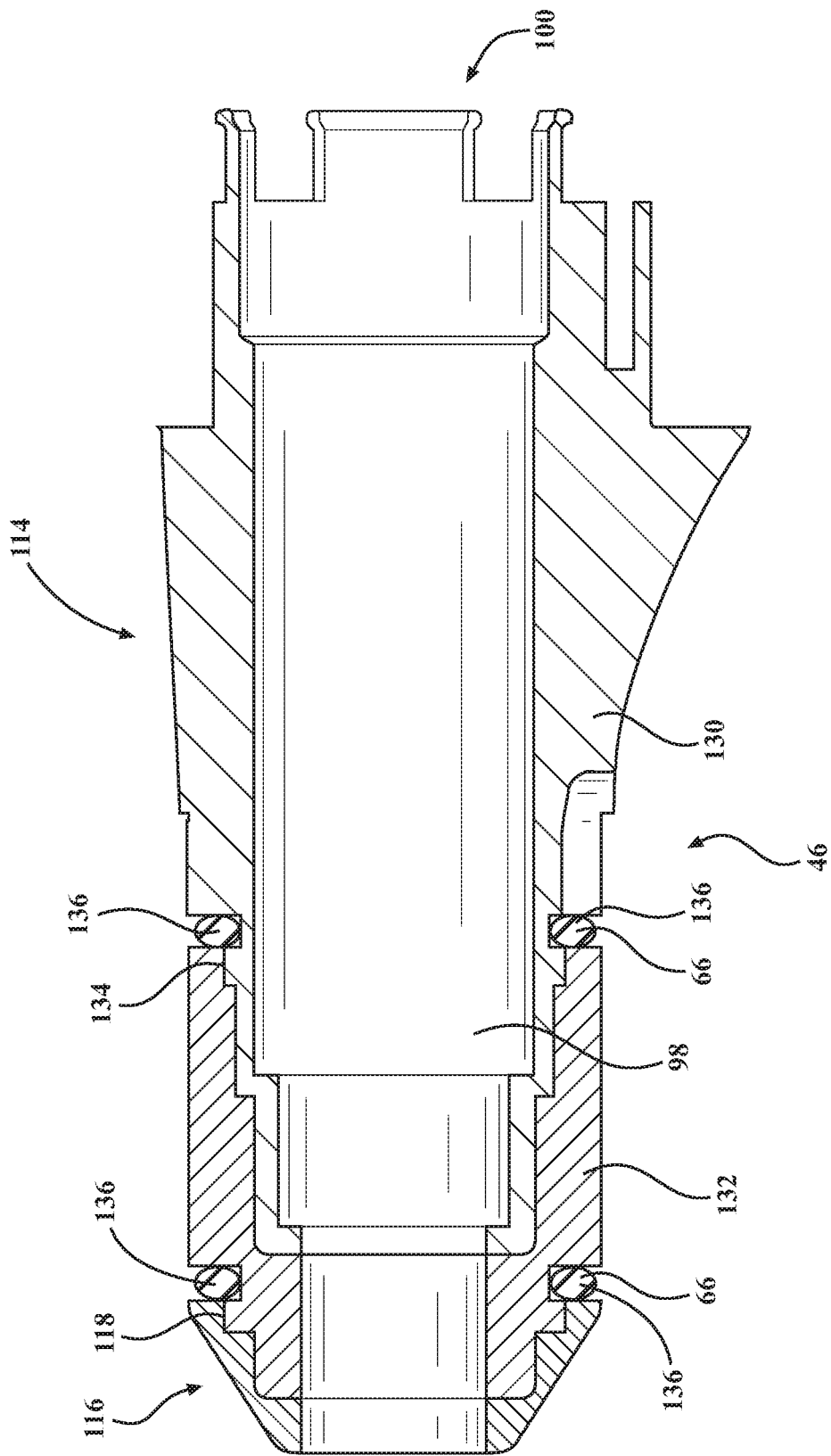
FIG. 13 is a sectional view of the hub of FIG. 12.

FIGS. 12 and 13 illustrate a perspective and sectional view, respectively, of the hub 46 wherein the first hub portion 114 comprises multiple hub parts, such as a first hub part 130 and a second hub part 132. The first hub part 130 is connected to the second hub part 132 to define a second hub joint 134. At least one annular sealing member 66 may be utilized to fluidly seal the first hub portion 114 to the second hub portion 116. Additionally, at least one annular sealing member 66 may be utilized to fluidly seal the first hub part 130 to the second hub part 132 at the second hub joint 134.

In some examples, the annular sealing member 66 may comprise a ring 136 configured to engage and fluidly seal the first hub portion 114 and the second hub portion 116 at the hub joint 118 to seal the hub joint 118. Furthermore, another ring 136 may be configured to engage and fluidly seal the first hub part 130 to the second hub part 132, as shown in FIGS. 12 and 13. In some examples, the ring 136 is an elastomeric ring configured to sealably secure the first hub portion 114 to the second hub portion 116 to prevent the egress of fluid from the hub 46. As described above, the fluid travelling from the housing 30 to the irrigation sleeve 48 experience the pressure drop and the increased resistance. The ring 136 engages and seals the first hub portion 114 to the second hub portion 116 to remain fluidly sealed to overcome the pressure drop and increased resistance. n some examples, the other ring 136 is an elastomeric ring configured to sealably secure the first hub part 130 to the second hub part 132 to further prevent the egress of fluid from the hub 46. The ring 136 may comprise one or more polymer, elastomer, fluoroelastomer (FKM), ethylene propylene, ethylene propylene diene monomer (EPDM), medical grade silicone, nitrile, combinations thereof, or any other suitable sealing materials.

In some configurations, it is contemplated that the first hub part 130, the second hub part 132, the first hub portion 114, and the second hub portion 116 may be sealably secured by any combination of annular sealing members 66. For example, the first hub portion 114 and the second hub portion 116 could be sealably secured by at least one ring 136 and at least one sealing sleeve 67, or any combinations thereof. Other forms of sealing members are also contemplated for use in the examples described herein. Furthermore, the annular sealing members 66 may be only partially annular or fully annular to only partially or fully surround the hub 46, and/or inner sheath 50, and/or outer sheath 58. Other shapes of the sealing members 66 are also contemplated.

Figure 14:
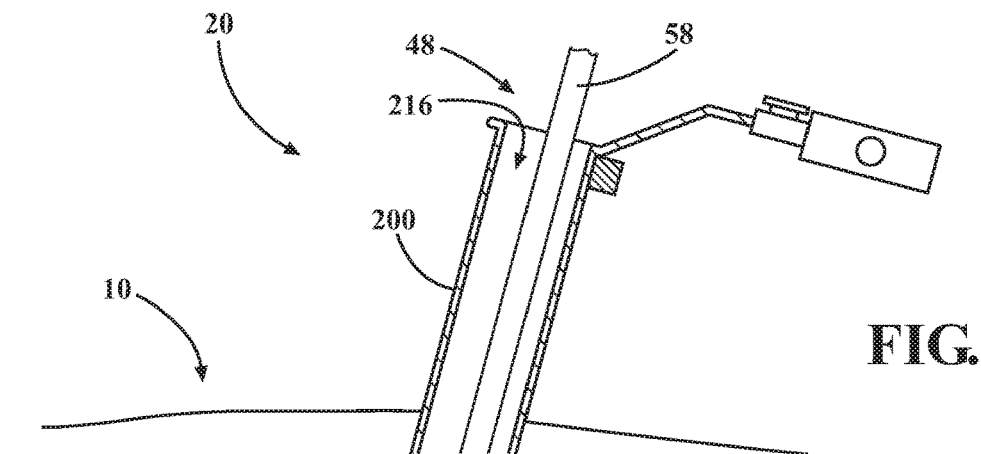
FIG. 14 is a schematic view of the ultrasonic surgical assembly of FIG. 1 including an irrigation sleeve and ultrasonic tip being inserted through an exemplary patient access portal defined by a dilator for spinal surgery.

Referring to FIG. 14, an exemplary arrangement of the ultrasonic surgical assembly 20 including an irrigation sleeve assembly 48 and ultrasonic tip 40 being utilized by a medical professional to remove/cut biological material 12A from a patient 10 is illustrated. In performing a medical procedure, such as minimally invasive surgery or keyhole surgery, the medical professional may insert at least a portion of the ultrasonic tip 40 and/or the irrigation sleeve assembly 48 of the ultrasonic surgical assembly 20 through an access portal 216 in the patient 10 in order to access the biological material that is to be cut and/or removed from the patient. The access portal 216 may comprise any type of opening in the patient 10 that provides access to the biological material 12A to be cut and/or removed by the ultrasonic surgical assembly 20. The access portal 216 may be formed using a dilator/retractor 200 to expand an existing opening. For example, as illustrated in FIG. 14, the medical professional may utilize a dilator 200 to create and/or define the access portal 216. As described above, the outer diameter of the outer sheath 58 of the irrigation sleeve assembly 48 may generally be configured to be seven (7) millimeters (mm) or less. The dilator 200 may be configured to define an access portal 216 having an inner diameter of approximately twenty (20) to twenty eight (28) millimeters (mm) to allow the ultrasonic surgical assembly 20 to access to the biological tissue 12A to be cut and/or removed while minimizing the opening defined/cut in the patient 10 to limit the impact to the patient 10 and reduce healing time.

Figure 15:
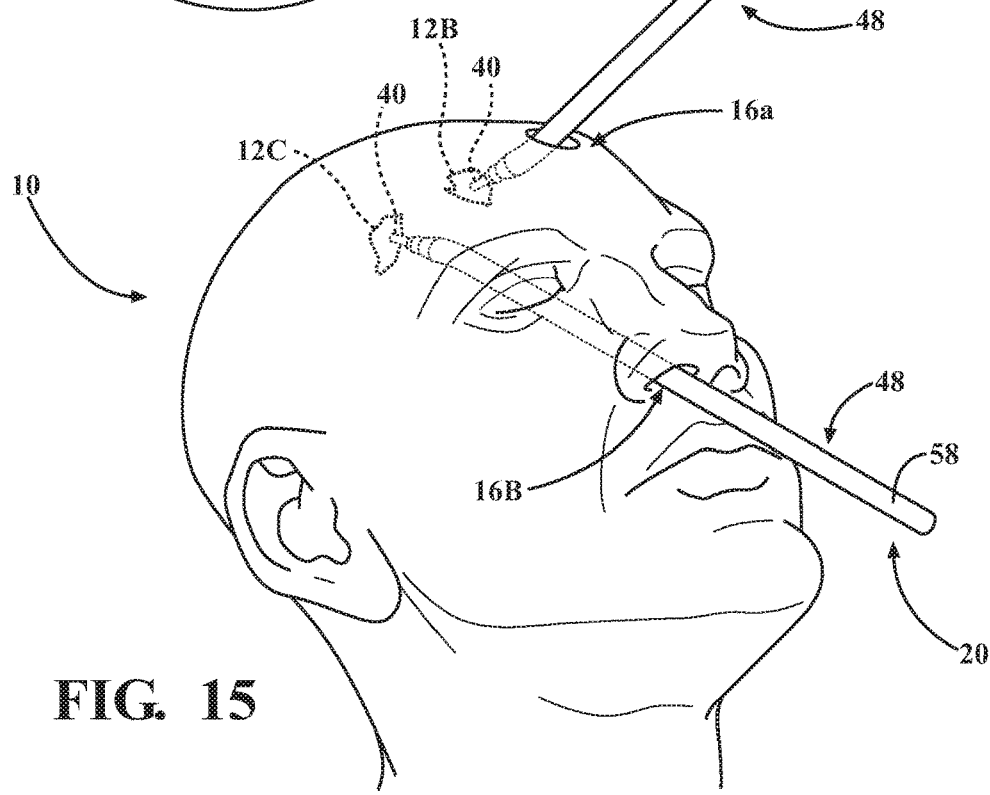
FIG. 15 is a perspective view of the ultrasonic surgical assembly of FIG. 1 including an irrigation sleeve and ultrasonic tip being inserted through alternative exemplary patient access portals in the patients skull for nasal surgery or neurosurgery.

Alternatively, it is also contemplated that the access portal 16A, 16B may cut in the patient using a high-speed bur or other similar medical cutting device. Referring to FIG. 15 variations of access portals 16A, 16B defined by cutting an opening in the cranium are illustrated. For example, a medical professional may utilize a high-speed bur to cut and access portal 16A in the posterior of the of the skull to provide access to a tumor 12B on the brain. Alternatively, the medical professional may utilize a high-speed bur to cut and access portal 16B through the patients 10 sinus cavity to provide access to a tumor 12C to be removed from the patients sinuses. It is contemplated that the access portal 16B may comprise an existing opening in the patient. For example, in the case of endonasal surgery, the access portal may comprise the patients nose and/or nasal cavities to access the patent's skull base. As described above, the outer diameter of the outer sheath 58 of the irrigation sleeve assembly 48 may generally be configured to be seven (7) millimeters (mm) or less. The high-speed bur may be utilized to cut/define an access portal 16A, 16B having an inner diameter of approximately twelve (12) to twenty (20) millimeters (mm) to allow the ultrasonic surgical assembly to access to the biological tissue to be cut and/or removed while minimizing the opening defined/cut in the patient to limit the impact to the patient and reduce healing time.

Method of using an ultrasonic surgical assembly having a cutting tip with a double lumen irrigation sleeve to perform minimally invasive surgery may comprise positioning the double lumen irrigation sleeve within an access portal of a patient. The double lumen irrigation sleeve may comprise an inner sheath at least partially disposed within an outer sheath and each of the inner sheath and the outer sheath may be coupled to a hub of the irrigation sleeve by an annular sealing member configured to create fluid-tight seal between the hub and the corresponding inner sheath and outer sheath. The method may further comprise cutting with the cutting tip while the double lumen irrigation sleeve is at least partially disposed within the access portal of the patient. The method may further comprise defining the access portal of the patient using a dilator. The dilator may have an inner diameter between 20 to 28 millimeters (mm). A larger or smaller dilator may be used if needed. The method may also comprise creating the access portal of the patient with a high-speed bur in a skull of the patient, wherein the access portal comprises a generally circular shape having an inner diameter between 10 to 20 millimeters (mm). It is also contemplated that the access portal may comprises a generally square, triangular, rectangular, or similar polygonal shape. Furthermore, the high-speed bur may be used to cut a smaller or larger access portal if needed. In yet another exemplary configuration, the cutting tip including a double lumen irrigation sleeve may be inserted through the access portal defined by said nasal and/or sinus cavity to execute and endo-nasal procedure. The irrigation sleeve may be configured such that the outer diameter of the outer sheath is seven millimeters (mm) or less.

Method of manufacturing a double lumen irrigation sleeve for use with an ultrasonic surgical instrument to perform minimally invasive surgery may comprise coupling an inner sheath to a hub the double lumen irrigation sleeve. The method may further comprise positioning a first annular sealing member such that the first annular sealing member is at least partially disposed over the hub and the inner sheath and applying a heat source to the first annular sealing member to define a fluid-tight seal between the hub and the inner sheath. The method may also comprise coupling an outer sheath to the hub of the double lumen irrigation sleeve, wherein the outer sheath defines a lumen and the inner sheath is at least partially disposed within the lumen. The method may further comprise positioning a second annular sealing member such that the second annular sealing member is at least partially disposed over the hub and the outer sheath and applying a heat source to the second annular sealing member to define a fluid-tight seal between the hub and the outer sheath. The inner sheath and outer sheath may define an irrigation passageway to deliver irrigation fluid to a surgical site. The hub may comprise an irrigation conduit in the hub of the irrigation sleeve that is in fluid communication with the irrigation passageway defined by the inner sheath and the outer sheath. The outer diameter of the outer sheath may be configured to be seven millimeters (mm) or less. Each of said first and said second annular sealing members may comprise a heat shrink material.

CLAUSES

I. An ultrasonic surgical assembly comprising:
 an ultrasonic instrument having a proximal end and a distal end, said ultrasonic instrument comprising:
  a housing comprising a proximal portion and a distal portion;
  a transducer at least partially disposed within said housing;
  a horn coupled to said transducer; and
  an ultrasonic tip comprising a shaft coupled to said horn; an irrigation sleeve assembly comprising:
  a hub releasably coupled to said distal portion of said housing; and
  an irrigation sleeve coupled to said hub, said irrigation sleeve comprising:
   an inner sheath extending distally from said hub, said inner sheath having a
   proximal end and an opposing distal end, and defining a lumen which at least partially surrounds said shaft of said ultrasonic tip;

an outer sheath extending distally from said hub, said outer sheath having a proximal end and an opposing distal end;

wherein said outer sheath surrounds a portion of said inner sheath to define an irrigation passageway between said outer sheath and said inner sheath; and wherein said irrigation passageway is configured to deliver irrigation fluid to a surgical site.

II. The ultrasonic surgical assembly of clause I, further comprising an annular sealing member configured to prevent egress of fluid from said hub.

III. The ultrasonic surgical assembly of clause II, wherein said hub comprises a first hub portion and a second hub portion connected to said first hub portion to define a hub joint, wherein said annular sealing member comprises a sealing sleeve at least partially surrounding said first hub portion and said second hub portion at said hub joint to seal said hub joint.

IV. The ultrasonic surgical assembly of clause III, wherein said outer sheath comprises an outer sheath flange engaging said second hub portion to define an outer sheath joint, wherein said annular sealing member at least partially surrounds said second hub portion and said outer sheath at said outer sheath joint to seal said outer sheath joint.

V. The ultrasonic surgical assembly of clause III or IV, wherein said inner sheath defines an inner sheath flange engaging said first hub portion to define an inner sheath joint, and said inner sheath joint is at least partially surrounded by said annular sealing member.

VI. The ultrasonic surgical assembly of clause II, wherein said hub comprises a first hub portion and a second hub portion connected to said first hub portion to define a hub joint, and wherein said annular sealing member comprises an elastomeric ring configured to engage said first hub portion and said second hub portion at said hub joint to seal said hub joint.

VII. The ultrasonic surgical assembly of any of clauses I to VI, further comprising an inner annular sealing member disposed in said hub to seal between said ultrasonic tip and said hub.

VIII. The ultrasonic surgical assembly of any of clauses I to VII, wherein said shaft comprises an aperture configured to be in fluid communication with said aspiration passageway, wherein said aperture is located proximal to said distal end of said inner sheath.

IX. The ultrasonic surgical assembly of any of clauses I to VIII, wherein said ultrasonic tip comprises a distal portion and an opposing proximal portion, wherein said distal portion of said ultrasonic tip bends relative to said proximal portion of said ultrasonic tip.

X. The ultrasonic surgical assembly of clause IX, wherein said irrigation sleeve has a bend corresponding to said distal portion of said ultrasonic tip.

XI. The ultrasonic surgical assembly of any of clauses I to X, wherein said irrigation sleeve is more flexible than said ultrasonic tip for positioning said irrigation sleeve over said ultrasonic tip.

XII. The ultrasonic surgical assembly of any of clauses I to IX and XI, wherein said outer sheath is configured to move radially independent of said inner sheath to maintain said irrigation passageway between said inner sheath and said outer sheath.

XIII The ultrasonic surgical assembly of any of clauses I to XII, wherein said inner sheath and said outer sheath of said irrigation sleeve assembly form an annular gap there between to define said irrigation passageway.

XIV. The ultrasonic surgical assembly of any of clause I to XIII, wherein said lumen of said inner sheath is sized to define a gap between said inner sheath and said ultrasonic tip.

XV. The ultrasonic surgical assembly of any of clause I to XIV, wherein said ultrasonic instrument defines an aspiration passageway.

XVI. A tool assembly comprising:
an ultrasonic tip; and
an irrigation sleeve assembly comprising:
a hub; and
an irrigation sleeve coupled to said hub, said irrigation sleeve comprising:
an inner sheath extending distally from said hub, said inner sheath having a proximal end and an opposing distal end, and defining a lumen which at least partially surrounds said shaft of said ultrasonic tip;
an outer sheath extending distally from said hub, said outer sheath having a proximal end and an opposing distal end;
wherein said outer sheath surrounds a portion of said inner sheath to define an irrigation passageway between said outer sheath and said inner sheath; and
wherein said irrigation passageway is configured to deliver irrigation fluid to a surgical site.

XVII. The tool assembly of clause XVI, further comprising an annular sealing member configured to prevent egress of fluid from said hub.

XVIII. The tool assembly of clause XVII, wherein said hub comprises a first hub portion and a second hub portion connected to said first hub portion to define a hub joint, wherein said annular sealing member comprises a sealing sleeve at least partially surrounding said first hub portion and said second hub portion at said hub joint to seal said hub joint.

XIX. The tool assembly of clause XVIII, wherein said outer sheath comprises an outer sheath flange engaging said second hub portion to define an outer sheath joint, wherein said annular sealing member at least partially surrounds said second hub portion and said outer sheath at said outer sheath joint to seal said outer sheath joint.

XX. The tool assembly of clause XVIII or XIX, wherein said inner sheath defines an inner sheath flange engaging said first hub portion to define an inner sheath joint, and said inner sheath joint is at least partially surrounded by said annular sealing member.

XXI. The tool assembly of clause XVII, wherein said hub comprises a first hub portion and a second hub portion connected to said first hub portion to define a hub joint, and wherein said annular sealing member comprises an elastomeric ring configured to engage said first hub portion and said second hub portion at said hub joint to seal said hub joint.

XXII. The tool assembly of any of clauses XVI to XXI, further comprising an inner annular sealing member disposed in said hub and configured to seal between said ultrasonic tip and said hub.

XXIII The tool assembly of any of clauses XVI to XXII, wherein said shaft comprises an aperture configured to be in fluid communication with said aspiration passageway, wherein said aperture is located proximal to said distal end of said inner sheath.

XXIV. The tool assembly of any of clauses XVI to XXIII, wherein said ultrasonic tip comprises a distal portion and an opposing proximal portion, wherein said distal portion bends relative to said proximal portion.

XXV. The tool assembly of clause XXIV, wherein said irrigation sleeve has a bend corresponding to said distal portion of said ultrasonic tip.

XXVI. The tool assembly of any of clauses XVI to XXIV, wherein said irrigation sleeve is more flexible than said ultrasonic tip for positioning said irrigation sleeve over said ultrasonic tip.

XXVII. The tool assembly of any of clauses XVI to XXIV and XXVI, wherein said outer sheath is configured to move radially independent of said inner sheath to maintain said irrigation passageway between said inner sheath and said outer sheath.

XXVIII. The tool assembly of any of clauses XVI to XXVII, wherein said lumen of said inner sheath is sized to define a gap between said inner sheath and said ultrasonic tip.

XXIX. The tool assembly of any of clauses XVI to XXVIII, wherein said inner sheath and said outer sheath of said irrigation sleeve assembly form an annular gap there between to define said irrigation passageway.

XXX. The tool assembly of any of clauses XVI to XXIX, wherein ultrasonic tip comprises a shaft defining an aspiration passageway.

XXXI. An ultrasonic surgical assembly comprising:
an ultrasonic instrument having a proximal end and a distal end, and defining an aspiration passageway, said ultrasonic instrument comprising:
a housing comprising a proximal portion and a distal portion;
a transducer at least partially disposed within said housing;
a horn coupled to said transducer; and
an ultrasonic tip comprising a shaft coupled to said horn;
an irrigation sleeve assembly comprising:
a hub releasably coupled to said distal portion of said housing; and
an irrigation sleeve coupled to said hub and configured to define an irrigation passageway is configured to deliver irrigation fluid to a surgical site, said irrigation sleeve comprising:
an inner sheath extending distally from said hub, said inner sheath having a proximal end and an opposing distal end, and defining a lumen configured to at least partially surround the ultrasonic tip; and
an annular sealing member surrounding at least a portion of said hub and said irrigation sleeve, and said annular sealing member configured to prevent egress of fluid from said hub and said irrigation sleeve.

XXXII. A tool assembly comprising:
an ultrasonic tip comprising:
a shaft defining an aspiration passageway; and
an irrigation sleeve assembly comprising:
a hub; and
an irrigation sleeve coupled to said hub and configured to define an irrigation passageway is configured to deliver irrigation fluid to a surgical site, said irrigation sleeve comprising:
an inner sheath extending distally from said hub, said inner sheath having a proximal end and an opposing distal end, and defining a lumen configured to at least partially surround the ultrasonic tip; and
an annular sealing member surrounding at least a portion of said hub and said irrigation sleeve, and said annular sealing member configured to prevent egress of fluid from said hub and said irrigation sleeve.

Several configurations have been discussed in the foregoing description. However, the configurations discussed herein are not intended to be exhaustive or limit the invention to any particular form. For example, while the example configurations describe the surgical tool as an ultrasonic surgical assembly, it is further contemplated that the features and concepts described with regard to the ultrasonic surgical assembly may be applied to other medical or surgical instruments. This similarly applies to the ultrasonic tip, which may further include blades, drill bits, rotating burs, open-window shavers, and the like. The terminology which has been used is intended to be in the nature of words of description rather than of limitation. Many modifications and variations are possible in light of the above teachings and the invention may be practiced otherwise than as specifically described.

The invention claimed is:

1. An irrigation sleeve assembly for use with an ultrasonic tip of an ultrasonic instrument, the irrigation sleeve assembly comprising:
a hub configured to be releasably coupled to the ultrasonic instrument, the hub including an irrigation conduit;
an inner sheath extending distally from the hub, the inner sheath coupled to the hub to create a fluid-tight seal between the inner sheath and the hub, the inner sheath defining a lumen configured to at least partially surround the ultrasonic tip; and
an outer sheath extending distally from the hub, the outer sheath coupled to the hub by a first annular sealing member comprising a heat shrink material and configured to create a fluid-tight seal between the outer sheath and the hub; and
a second annular sealing member disposed at a proximal end of the inner sheath and configured to create the fluid-tight seal between the inner sheath and the hub, the second annular sealing member comprising a heat shrink material,
wherein the outer sheath is configured to surround a portion of the inner sheath to define an irrigation passageway between the outer sheath and the inner sheath that is in fluid communication with the irrigation conduit of the hub to deliver irrigation fluid to a surgical site.

2. The irrigation sleeve assembly of claim 1, wherein at least a portion of the second annular sealing member is disposed over the inner sheath and the hub.

3. The irrigation sleeve assembly of claim 1, wherein the inner sheath defines an inner sheath flange engaging the hub to define an inner sheath joint sealed by the second annular sealing member.

4. The irrigation sleeve assembly of claim 1, wherein the first annular sealing member comprises a sealing sleeve at least partially surrounding the hub and the outer sheath to seal the outer sheath to the hub.

5. The irrigation sleeve assembly of claim 1, wherein the outer sheath comprises an outer sheath flange engaging the hub to define an outer sheath joint, and the first annular sealing member at least partially surrounds the hub and the outer sheath to seal the outer sheath joint.

6. The irrigation sleeve assembly of claim 5, wherein the hub defines a collar engaging the outer sheath flange to define the outer sheath joint.

7. The irrigation sleeve assembly of claim 5, wherein the inner sheath is coupled to the hub by a second annular sealing member configured to create a fluid-tight seal between the inner sheath and the hub.

8. The irrigation sleeve assembly of claim 1, wherein the inner sheath is more flexible than the outer sheath.

9. The irrigation sleeve assembly of claim 1, wherein the inner and outer sheaths each have a bend corresponding to a bend in the ultrasonic tip.

10. The irrigation sleeve assembly of claim 1, wherein the inner and outer sheaths are more flexible than the ultrasonic tip for positioning the irrigation sleeve assembly over the ultrasonic tip.

11. The irrigation sleeve assembly of claim 1, wherein the outer sheath is configured to move radially independently of the inner sheath to maintain the irrigation passageway between the inner sheath and the outer sheath.

12. The irrigation sleeve assembly of claim 1, wherein the lumen of the inner sheath is sized to define a gap between the inner sheath and the ultrasonic tip.

13. The irrigation sleeve assembly of claim 1, further comprising an inner seal disposed within the hub and configured to seal between the hub and the ultrasonic tip.

14. The irrigation sleeve assembly of claim 1, wherein an outer diameter of the outer sheath is seven millimeters or less.

15. The irrigation sleeve assembly of claim 1, wherein a distal portion of the outer sheath is positioned distally of a distal end of the inner sheath.

16. A tool assembly comprising:
an ultrasonic tip; and
the irrigation sleeve assembly of claim 1.

17. The tool assembly of claim 16, further comprising an inner annular sealing member disposed in the hub and configured to seal between the ultrasonic tip and the hub.

18. The assembly of claim 16, wherein the ultrasonic tip includes a shaft defining an aspiration passageway, and
wherein the shaft comprises an aperture configured to be in fluid communication with the aspiration passageway, the aperture positioned on the shaft to be proximal to a distal end of the inner sheath.

19. The assembly of claim 18, wherein a distal portion of the outer sheath is positioned distally of a distal end of the inner sheath.

20. An ultrasonic surgical assembly comprising:
an ultrasonic instrument having a proximal end and a distal end, the ultrasonic instrument comprising:
a housing comprising a proximal portion and a distal portion,
a transducer at least partially disposed within the housing,
a horn coupled to the transducer, and
an ultrasonic tip coupled to the horn; and
the irrigation sleeve assembly of claim 1, the hub of the irrigation sleeve assembly releasably coupled to the distal portion of the housing.

\* \* \* \* \*